United States Patent [19]
Kelley et al.

[11] Patent Number: 5,662,732
[45] Date of Patent: Sep. 2, 1997

[54] POLISH COMPOSITION

[75] Inventors: Julie A. Kelley, Huntington Valley; Susan M. Grillo, Lansdale, both of Pa.

[73] Assignee: BPSI Holdings, Inc., Wilmington, Del.

[21] Appl. No.: 689,398

[22] Filed: Aug. 9, 1996

[51] Int. Cl.$^6$ ..................................................... A61K 9/42
[52] U.S. Cl. ....................... 106/271; 427/2.2; 427/2.14; 427/212; 426/305; 424/476
[58] Field of Search ........................ 106/271; 426/305; 424/476; 427/2.2, 2.14, 212

[56] References Cited

U.S. PATENT DOCUMENTS 5,389,129  2/1995  Jordan ......................................... 106/10
5,593,682  1/1997  Papas et al. ............................. 424/401

*Primary Examiner*—Melissa Bonner
*Attorney, Agent, or Firm*—John F. A. Earley; John F. A. Earley, III

[57] ABSTRACT

A wax polish composition for coating pharmaceutical tablets and food/confectionery items to impart gloss thereto, comprises wax, water, and an emulsifier, the emulsifier comprising a combination of polyoxyethylene 80 sorbitan monolaurate and acetylated monoglyeride, the emulsifier being in a range of about 9.46% to 9.60% by weight of the composition, and the emulsifier having an HLB value of about 9.45.

20 Claims, No Drawings

POLISH COMPOSITION

BACKGROUND OF THE INVENTION

1. Field of the Invention

This invention relates to a wax polish composition, such as a wax polish composition for pharmaceutical tablets and food/confectionery pieces.

2. Description of the Prior Art

Conventional wax polish compositions are solutions of wax in an organic solvent such as carbon tetrachloride or ether. However, these solvents give rise to processing problems in the application of the polish to pharmaceutical tablets or confectionery pieces. For example, the removal of waste organic solvent vapor formed during the polishing process from exhaust air streams is very expensive, and an increasing number of countries do not allow vapors of organic solvents to be vented directly into the atmosphere. Further, many organic solvents are dangerous fire hazards and toxicity hazards to process workers. Moreover, inadvertent over-use of such wax solutions may spoil the product by the adhesion of excess wax to the surface.

If conventional wax polishing is performed in the presence of water, the surface of the tablet or piece to which the wax polish has been applied is usually subjected to overwashing which causes spoiling of the tablet's surface.

Because of the problems associated with the use of organic solvents, Colorcon developed an aqueous wax polish composition which is disclosed in Jordon U.S. Pat. No. 5,389,129 which issued on Feb. 14, 1995 and which is incorporated herein by reference. The aqueous wax polish composition disclosed in U.S. Pat. No. 5,389,129 provides an excellent wax coating for coating pharmaceutical tablets and food/confectionery items to impart a gloss thereto without dissolving the surface of the substrate with resultant deleterious effects on the finished product appearance. However, this aqueous polish composition may thicken during storage under certain conditions when stored for a long period of time.

SUMMARY OF THE INVENTION

It is an object of the invention to provide a wax polish composition which overcomes the problems associated with wax polish compositions based on organic solvents.

Another object of the invention is to provide a wax polish composition that is stable and fluid, even after a year after being manufactured.

These and other objects are accomplished by our invention, which is described below.

DETAILED DESCRIPTION OF THE INVENTION

A wax polish composition for coating pharmaceutical tablets and food/confectionery items to impart gloss thereto comprises wax, water, and an emulsifier.

The wax comprises carnauba wax, beeswax, or a combination of carnauba wax and beeswax, and the wax comprises about 40% by weight of the wax polish composition. Preferably, carnauba wax-and beeswax are present in the wax polish composition in substantially equal amounts.

The water is present in an amount of about 50% by weight of the wax polish composition.

The emulsifier comprises a combination of polyoxyethylene 80 sorbitan monolaurate (Polysorbate 80) (commercially available from ICI Americas Inc. under the trademark Tween 80) and acetylated monoglyeride (commercially available from Eastman under the trademark Myvacet 945). The emulsifier is effective and suitable for dispersing the components of the emulsion. The emulsifier is present in a range of about 9.46% to about 9.60% by weight of the wax polish composition. The emulsifier has a hydrophile-lipophile balance value ("HLB value") of about 9.45. That is, the combined HLB value obtained by combining the HLB value for polyoxyethylene 80 sorbitan monolaurate with the HLB value for the acetylated monoglyeride is about 9.45.

Optionally, but preferably, the wax polish composition of the present invention may contain a preservative, preferably in an amount of about 0.2% by weight of the wax polish composition. Sorbic acid is the preferred preservative.

The wax polish composition of the invention may be made by heating the wax and water together, preferably to around 90° C., to melt the wax. After the wax is melted, the emulsifier is stirred, preferrably with a high shear mixer, into the mixture of wax and water, and the mixture of wax, water, and emulsifier is cooled to about 60° C. while stirring continues, preferably with a high shear mixer. Then, the preservative (e.g., sorbic acid) may be added to the mixture of wax, water, and emulsifier, while continuing stirring and cooling. Although the polyoxyethylene 80 sorbitan monolaurate and acetylated monoglyeride may be added individually to the wax and water, preferably, the polyoxyethylene 80 sorbitan monolaurate and the acetylated monoglyeride are mixed together to form a emulsifier mixture, and this emulsifier mixture is added to the melted wax and solvent.

Alternatively, melted wax with the emulsifier is added to hot water, and the mixture cooled with stirring to form a stable emulsion.

The invention will now be described further with reference to the following examples:

EXAMPLE 1

The following components comprise a formulation of the invention:

| Component | Grams | Percent by Weight |
| --- | --- | --- |
| beeswax | 20.06 | 20.06 |
| carnauba wax | 20.06 | 20.06 |
| purified water | 50.10 | 50.10 |
| Tween 80 | 4.795 | 4.795 |
| Myvacet 945 | 4.795 | 4.795 |
| sorbic acid | 0.19 | 0.19 |
| | 100.00 | 100% |

Using a cooker/chiller with high shear and agitation capabilities (e.g., a Lee cooker equipped with a high shear stirrer), 20.06 grams of beeswax, 20.06 grams of carnauba wax, and 50.11 grams of purified water are heated together to about 90° C. to melt the beeswax and the carnauba wax in the water. After all of the wax is melted, a pre-mixed emulsifier mixture of 4.795 grams of Tween 80 and 4.795 grams of Myvacet 945 is stirred into the mixture of wax and water using a high shear stirrer, and while continuing high shear stirring, the resulting mixture of wax, water and emulsifier is cooled rapidly to 60° C. Then, while continuing stirring and cooling, 0.19 grams of sorbic acid is stirred into the mixture of wax, water, and emulsifier. The product is a stable and fluid wax-in-water emulsion.

The following Examples 2–4, which show different formulations of the invention, further illustrate the invention. In each Example 2–4, a stable and fluid wax-in-water emulsion is made using the procedure of Example 1, except that the amounts of each component used in the emulsion of each example correspond to the specific formulation given for each example.

EXAMPLE 2

| Component | Grams | Percent by Weight |
|---|---|---|
| beeswax | 20.06 | 20.06 |
| carnauba wax | 20.06 | 20.06 |
| purified water | 50.11 | 50.11 |
| Tween 80 | 4.79 | 4.79 |
| Myvacet 945 | 4.79 | 4.79 |
| sorbic acid | 0.19 | 0.19 |
|  | 100.00 | 100% |

EXAMPLE 3

| Component | Grams | Percent by Weight |
|---|---|---|
| beeswax | 20.08 | 20.08 |
| carnauba wax | 20.08 | 20.08 |
| purified water | 50.19 | 50.19 |
| Tween 80 | 4.73 | 4.73 |
| Myvacet 945 | 4.73 | 4.73 |
| sorbic acid | 0.19 | 0.19 |
|  | 100.00 | 100% |

EXAMPLE 4

| Component | Grams | Percent by Weight |
|---|---|---|
| beeswax | 20.06 | 20.06 |
| carnauba wax | 20.06 | 20.06 |
| purified water | 50.08 | 50.08 |
| Tween 80 | 4.80 | 4.80 |
| Myvacet 945 | 4.80 | 4.80 |
| sorbic acid | 0.20 | 0.20 |
|  | 100.00 | 100% |

The polish compositions of the present invention may be used to coat tablets with a layer of wax to impart a gloss to the tablet surface, and any of the conventional tablet coating methods may be used, including conventional round or hexagonal sugar coating pans, canvas-lined pans, side-vented coating pans, and continuous coating pans. Further, the inventive composition may be applied to pharmaceutical tablets and food/confectionery items using a simple ladling technique, in which a sufficient volume of the composition to cover the surface of the tablets or food/confectionery items being polished is poured over those tablets or food/confectionery items as they are being agitated by rotation of the aforementioned equipment. Drying air and exhaust ventilation may be employed to promote drying of the composition.

The composition may be used as a single application or it may be preferably divided into two or more applications with intervening drying steps. Once an even layer of wax has been deposited, the tablets or food/confectionery items continue to be rolled in the equipment until the required gloss develops.

As an alternative to the ladling technique, the composition may be applied to the tablets and food/confectionery items in the form of a fine spray, using either air-atomized or airless technology, in the same type of coating equipment as specified above. Spraying is continued until an even layer of wax is deposited and then rotation continued until the required gloss develops.

Pharmaceutical tablets and food/confectionery items which are traditionally subjected to a wax polishing process, generally have water soluble surfaces. Without careful formulation, an aqueous polishing agent tends to dissolve the existing surface with resultant deleterious effects on the finished product appearance and possibly, stability. The present invention overcomes these problems by binding the water to the wax until it is lost by evaporation in the polishing pan.

The polish compositions of the present invention are applied to pharmaceutical tablets, including sugar coated tablets, and food/confectionery pieces to give a wax layer which is polishable without damage to the surfaces of the pharmaceutical tablets and food/confectionery pieces.

We claim:

1. A wax polish composition for coating pharmaceutical tablets and food/confectionery items to impart gloss thereto, comprising wax, water, and an emulsifier, the emulsifier comprising a combination of polyoxyethylene 80 sorbitan monolaurate and acetylated monoglyeride, the emulsifier being in a range of about 9.46% to 9.60% by weight of the composition, and the emulsifier having an HLB value of about 9.45.

2. The wax polish composition of claim 1, the wax comprising a combination of carnauba wax and beeswax.

3. The wax composition of claim 1, the wax being present in an amount of about 40% by weight of the composition.

4. The wax polish composition of claim 2, the carnauba wax and the beeswax being present in substantially equal amounts.

5. The wax polish composition of claim 1, the water being present in an amount of about 50% by weight of the composition.

6. The wax polish composition of claim 1, further including a preservative.

7. The wax polish composition of claim 6, the preservative being sorbic acid.

8. The wax polish composition of claim 6, the preservative being present in an amount of about 0.2% by weight of the composition.

9. The wax polish composition of claim 1, further including a preservative, the wax comprising a combination of carnauba wax and beeswax, the wax being present in an amount of about 40% by weight of the composition, the carnauba wax and the beeswax being present in substantially equal amounts, the water being present in an amount of about 50% by weight of the composition, the preservative being sorbic acid, and the sorbic acid being present in an amount of about 0.2% by weight of the composition.

10. A method of coating pharmaceutical tablet substrates or food/confectionery substrates with a layer of wax to impart a gloss thereto, comprising the steps of adding wax to a solvent, the solvent comprising water, heating the wax and solvent until the wax has melted, adding an emulsifier to the melted wax and solvent, the emulsifier comprising a combination of polyoxyethylene 80 sorbitan monolaurate and acetylated monoglyeride, the emulsifier being in a range of about 9.46% to 9.60% by weight of the combination of wax, the solvent, and the emulsifier, and the emulsifier having an HLB value of about 9.45, cooling and stirring the wax, solvent, and emulsifier until the temperature drops to about 60° C. or less to obtain a polish composition, applying an effective amount of the polish composition onto each substrate to form a polish coating on each substrate, drying the polish coating on each substrate, and buffing the polish coating on each substrate to impart a gloss thereto.

11. The method of claim 10, further including mixing the polyoxyethylene 80 sorbitan monolaurate and acetylated monoglyeride together prior to adding the emulsifier to the melted wax and solvent.

12. The method of claim 10, the wax comprising a combination of carnauba wax and beeswax.

13. The method of claim 10, the wax being present in an amount of about 40% by weight of the composition.

14. The method of claim 12, the carnauba wax and the beeswax being present in substantially equal amounts.

15. The method of claim 10, the water being present in an amount of about 50% by weight of the composition.

16. The method of claim 10, further including adding a preservative to the polish composition after it has been cooled to about 60° C.

17. The method of claim 16, the preservative being sorbic acid.

18. The method of claim 16, the preservative being present in an amount of about 0.2% by weight of the composition.

19. The method of claim 10, further including adding a preservative to the polish composition after it has been cooled to about 60° C., the wax comprising a combination of carnauba wax and beeswax, the wax being present in an amount of about 40% by weight of the composition, the carnauba wax and the beeswax being present in substantially equal amounts, the water being present in an amount of about 50% by weight of the composition, the preservative being sorbic acid, and the sorbic acid being present in an amount of about 0.2% by weight of the composition.

20. The method of claim 10, further including mixing the polyoxyethylene 80 sorbitan monolaurate and acetylated monoglyeride together prior to adding the emulsifier to the melted wax and solvent, adding a preservative to the polish composition after it has been cooled to about 60° C., the wax comprising a combination of carnauba wax and beeswax, the wax being present in an amount of about 40% by weight of the composition, the carnauba wax and the beeswax being present in substantially equal amounts, the water being present in an amount of about 50% by weight of the composition, the preservative being sorbic acid, the sorbic acid being present in an amount of about 0.2% by weight of the composition.

* * * * *